United States Patent
Sun et al.

(10) Patent No.: US 9,700,040 B2
(45) Date of Patent: Jul. 11, 2017

(54) POLYMERIC SYSTEMS FOR DELIVERING HYPOHALIDE SALTS

(75) Inventors: Yuyu Sun, Sioux Falls, SD (US); Zhengbing Cao, Sioux Falls, SD (US); Simon Johnston, Bellevue, WA (US)

(73) Assignee: The University of South Dakota, Vermillion, SD (US)

( * ) Notice: Subject to any disclaimer, the term of this patent is extended or adjusted under 35 U.S.C. 154(b) by 638 days.

(21) Appl. No.: 13/574,467

(22) PCT Filed: Jan. 20, 2011

(86) PCT No.: PCT/US2011/021832
§ 371 (c)(1),
(2), (4) Date: Dec. 18, 2012

(87) PCT Pub. No.: WO2011/091118
PCT Pub. Date: Jul. 28, 2011

(65) Prior Publication Data
US 2013/0115259 A1    May 9, 2013

Related U.S. Application Data

(60) Provisional application No. 61/297,129, filed on Jan. 21, 2010.

(51) Int. Cl.
*A01N 25/34* (2006.01)
*A01N 25/10* (2006.01)
*A01N 59/00* (2006.01)
*C01B 11/06* (2006.01)
*C01B 11/20* (2006.01)
*D06M 11/07* (2006.01)
*D06M 15/233* (2006.01)
*D06M 15/263* (2006.01)
*D06M 15/55* (2006.01)
*D06M 15/564* (2006.01)
*D06M 23/08* (2006.01)
*D06M 23/12* (2006.01)

(52) U.S. Cl.
CPC ............ *A01N 25/10* (2013.01); *A01N 59/00* (2013.01); *C01B 11/068* (2013.01); *C01B 11/20* (2013.01); *D06M 11/07* (2013.01); *D06M 15/233* (2013.01); *D06M 15/263* (2013.01); *D06M 15/55* (2013.01); *D06M 15/564* (2013.01); *D06M 23/08* (2013.01); *D06M 23/12* (2013.01)

(58) Field of Classification Search
CPC ...... A01N 25/10; A01N 59/00; C01B 11/068; C01B 11/20; D06M 11/07; D06M 15/233; D06M 15/263; D06M 15/55; D06M 15/564; D06M 23/08; D06M 23/12
See application file for complete search history.

(56) References Cited

U.S. PATENT DOCUMENTS

| | | | |
|---|---|---|---|
| 2,730,427 A * | 1/1956 | Suen ............................ | 8/120 |
| 3,063,869 A * | 11/1962 | Roth ............................ | 442/107 |
| 3,684,722 A | 8/1972 | Hynam et al. | |
| 4,167,561 A | 9/1979 | Lamberti et al. | |
| 4,457,855 A | 7/1984 | Sudbury et al. | |
| 4,756,844 A | 7/1988 | Walles et al. | |
| 5,460,743 A | 10/1995 | Delwel et al. | |
| 5,834,414 A | 11/1998 | Sowle et al. | |
| 5,985,302 A | 11/1999 | Dorr et al. | |
| 6,776,926 B2 | 8/2004 | Martin | |
| 2005/0279971 A1 | 12/2005 | Garris | |
| 2006/0147847 A1 | 7/2006 | Guire et al. | |
| 2007/0062884 A1 | 3/2007 | Sun et al. | |
| 2007/0238634 A1 * | 10/2007 | Foland et al. ............ | 510/406 |
| 2009/0318659 A1 | 12/2009 | Chang et al. | |

FOREIGN PATENT DOCUMENTS

| | | |
|---|---|---|
| JP | 2005248367 A | 9/2005 |
| WO | WO9747685 A1 | 12/1997 |

OTHER PUBLICATIONS

Braun, Martha et al., "Antimicrobial Polymers Containing Melamine Derivatives. I. Preparation and Characterization of Chloromelamine-Based Cellulose", J. Polym. Sci. Part A: Polym. Chem, 2004, 42, 3818-3827.

Chen, Zhaobin et al., Antimicrobial Polymers Containing Melamine Derivatives. II. Biocidal Polymers Derived from 2-Vinyl-4,6-diamino-1,3,5-triazine.

International Search Report and Written Opinion issued in PCT/US2011/021832, mailed Jun. 30, 2011, 14 pages.

Chen, Zhaobin, Sun, Yuyu, Antimicrobial Polymers Containing Melamine Derivatives II, Biocidal Polymers Derived From 2-Vinyl-4, 6-Diamini-1,3,5-Triazine, Journal of Polymer Science, Part A, Polymer Chemistry, vol. 43, 2005, pp. 4089-4095, Wiley Periodicals, Inc.

Sun, Yuyu, Preperation and Physical and Antimicrobial Properties of a Cellulose-Supported Chloromelamine Derivative, Industrial and Engineering Chemistry Research, No. 44, 2005, pp. 7916-7920.

* cited by examiner

*Primary Examiner* — David Browe

(57) ABSTRACT

The invention relates to polymeric systems for stabilizing, storing and delivering hypohalide salts. One system consists of material coated with two layers: one prepared from polyethylene glycol epoxide and melamine solution and second prepared from inorganic hypohalide salt solution. The material can be fabric, cotton, bamboo, cellulosic materials, blend of cellulosic and synthetic fibers. Antimicrobial materials comprising this system are also described. Another system consists of material containing pre-formed spaces coated with water-polyethylene glycol solution of hypohalide salt and encapsulated by film forming polymer. Hypohalide salts within both systems are in some cases storage stable for at least three months.

13 Claims, No Drawings

POLYMERIC SYSTEMS FOR DELIVERING HYPOHALIDE SALTS

CROSS-REFERENCE TO RELATED APPLICATION

This application claims the benefit of provisional patent application Ser. No. 61/297,129, entitled "POLYMERIC SYSTEMS FOR DELIVERING HYPOHALIDE SALTS" filed Jan. 21, 2010, which application is incorporated by reference herein in its entirety.

TECHNICAL FIELD

The disclosure pertains generally to inorganic hypochlorite and hypobromite salts and more particularly to polymeric delivery systems for solid hypochlorite and hypobromite salts.

BACKGROUND

Inorganic hypochlorite salts such as (sodium hypochlorite and calcium hypochlorite) and hypobromide salts such as (sodium hypobromide and calcium hypobromide) are excellent disinfecting agents with proven efficacy against a broad range of microorganisms and outstanding safety records. However, in general practice, these salts can be difficult to handle, store, transport, and/or apply. In some cases, these materials have poor storage stability, and thus normally have a short shelf life. If exposed to the atmosphere, the shelf life of these materials may be measured in days or even hours. In some cases, these salts are either dissolved in solution or are in solid particle or tablet forms that are not easily used in many applications.

SUMMARY

An embodiment of the invention is found in a method of delivering storage stable hypohalide salts in which a material is contacted with a first aqueous solution that includes polyethylene glycol epoxide and melamine. The first aqueous solution is dried on the material. The material is contacted with a second aqueous solution that includes hypohalide salts and is dried. The hypohalide salts in the material are stable for at least three months when exposed to atmosphere. In some embodiments, the resulting material retains, after three months of atmospheric contact, at least about 90 percent of the originally retained hypohalide salt.

Another embodiment of the invention is found in a method of delivering storage stable hypohalide salts in which a plurality of materials that include pre-formed spaces are contacted with an aqueous solution that includes hypohalide salts and polyethylene glycol to form hypohalide salt-containing materials with pre-formed spaces. These materials are added into a solution of a film forming polymer and a solvent to form a film-forming mixture. Evaporating the solvent from the film-forming mixture forms a film that contains the hypohalide salt-containing materials. The hypohalide salts in the film are stable for at least about three months when exposed to atmosphere.

Another embodiment of the invention is found in an antimicrobial material that includes a first coating that is formed on the material by contacting the material with an aqueous solution of polyethylene glycol epoxide and melamine. A second coating including a hypohalide is formed on the first coating. The hypohalide is stable for at least three months.

While multiple embodiments are disclosed, still other embodiments of the invention will become apparent to those skilled in the art from the following detailed description, which shows and describes illustrative embodiments of the invention. Accordingly, the detailed description are to be regarded as illustrative in nature and not restrictive.

DETAILED DESCRIPTION

The disclosure provides for improved stability and storage of inorganic hypohalide salts such as hypochlorite and hypobromide salts. In some embodiments, the disclosure provides water-insoluble polymeric systems for stabilizing, storing, carrying and delivering inorganic hypohalide salts. Examples of water-insoluble polymeric systems include but are not limited to fabrics, sheets, beads, coatings and the like.

The polymeric system includes materials such as articles, compounds and/or functional groups that can absorb and stabilize hypochlorite salts (such as sodium hypochlorite and calcium hypochlorite) and/or hypobromide salts (such as sodium hypobromide and calcium hypobromide). Examples of these materials include but are not limited to materials that include preformed spaces as well as materials that include resins or adhesives. Examples of materials including preformed spaces include substrates, hollow fibers, foams, encapsulates, hollow or porous inorganic or polymeric beads, zeolites, fibers, non-woven materials and the like. In some embodiments, the materials may be cellulosic, synthetic or combinations of cellulosic and synthetic.

In some embodiments, fibers may be considered to be networks of natural or artificial threads or yarns that are formed by weaving, knitting, crocheting, knotting or pressing fibers together. The individual fibers may be formed by spinning raw materials such as wool, linen, cotton, nylon, polyester, acrylics, polypropylene, polyethylene, polyvinyl chloride (PVC) or other materials on a spinning wheel to produce the fibers. Examples of materials including resins or adhesives include epoxide resins, melamine adhesives or resins, acrylic emulsions or resins, polyurethane resins or emulsions, and combinations thereof.

In some embodiments, these materials are dipped into or sprayed with solutions or powders of the hypochlorite salts such as sodium hypochlorite and calcium hypochlorite, and/or hypobromide salts such as sodium hypobromide and calcium hypobromide. Subsequently, the materials are coated, impregnated, absorbed, laminated, covalently bonded to and/or mixed with an inert polymeric matrix to form a polymeric system for carrying, stabilizing and delivering the inorganic hypochlorite and/or hypobromide salts.

In some embodiments, the materials including the aforementioned articles, compounds and/or functional groups are coated, impregnated, absorbed, laminated, covalently bound onto, and/or mixed with an inert polymeric matrix to form a polymeric system that is then dipped into or sprayed with a solution or powder of the inorganic hypochlorite and/or hypobromide salts.

In either approach, the inorganic hypochlorite salts such as (sodium hypochlorite and calcium hypochlorite) and hypobromide salts such as (sodium hypobromide and calcium hypobromide) in the resultant polymer systems have the same antimicrobial/disinfecting potentials that they have in solution, powder or tablet forms. However, the shelf life in the new polymeric systems is substantially improved over that of the solution, powder or tablet forms, being measurable in weeks or even years. Moreover, the polymeric systems are much easier to handle, store, transport, and/or apply/use in many antimicrobial/disinfecting applications.

In some embodiments, a piece of fabric is contacted with a first aqueous solution that includes polyethylene glycol epoxide and melamine, and the first aqueous solution is allowed to dry on the fabric. In some embodiments, the fabric may dipped into and/or sprayed with the first aqueous solution. The fabric may be contacted with a second aqueous solution that includes an acrylic material and a hypohalide salt such as sodium hypochlorite, and the second aqueous solution is allowed to dry. In some embodiments, the fabric may be sprayed with the second aqueous solution.

In some cases, the fabric may be contacted with the first aqueous solution before being contacted with the second aqueous solution. In some instances, the fabric may be contacted with the second aqueous solution before being contacted with the first aqueous solution. In some embodiments, the first aqueous solution may also include a water-based resin or adhesive. The hypohalide salt may be stable for at least three months when exposed to atmosphere.

In some embodiments, a plurality of porous beads may be contacted with an aqueous solution that includes a hypohalide salt such as sodium hypochlorite and polyethylene glycol to form hypohalide salt-containing beads. The beads may then be added into a solution of a film forming polymer and a solvent to form a film-forming mixture. The solvent may be evaporated from the film-forming mixture to form a film that includes the hypohalide salt-containing beads. The hypohalide salt in the film may be stable for at least three months when exposed to atmosphere.

In some embodiments, the porous beads may include beads having a particle size of about 300 to about 1200 microns and an average pore size of about 100 Angstroms. In some cases, the porous beads may include poly(4-ethylstyrene-co-divinylbenzene) beads.

In some embodiments, the aqueous solution may include about 0.01 to about 30 weight percent of hypohalide salt. In some embodiments, the aqueous solution may include about 1 to about 10 weight percent of hypohalide salt. In some embodiments, the aqueous solution may include about 10 weight percent of the sodium hypohalide salt.

In some embodiments, the solution of a film forming polymer and a solvent may include about 0.01 to about 40 weight percent of the film forming polymer, with the balance being the solvent. In some cases, the solution may include about 15 weight percent of the film forming polymer, with the balance being the solvent. In some embodiments, the solution may include about 0.1 to about 5 weight percent of the film forming polymer. In some embodiments, the film forming polymer may include ethylene vinyl acetate and the solvent may include dichloromethane.

In some embodiments, an antimicrobial fabric such as a cellulosic material may include free hydroxyl, amino, amide or carboxylate functional groups. A first coating may be formed on the fabric by contacting the fabric with an aqueous solution including polyethylene glycol epoxide and melamine. A second coating including a hypohalide such as sodium hypochlorite may be formed on the first coating. The hypohalide may be stable for at least about three months.

In some embodiments, the aqueous solution includes about 0.1 to about 30 grams of polyethylene glycol epoxide and about 0.01 to about 10 grams melamine per each about 100 milliliters of solution. In some embodiments, the aqueous solution includes about 2 to about 5 grams of polyethylene glycol epoxide and about 0.5 to about 2 grams melamine per each about 100 milliliters of solution. In some embodiments, the second coating is formed by contacting the first coating with an aqueous solution of hypohalide salt and optionally an acrylic material.

In some embodiments, an antimicrobial bamboo fabric may include a fabric made from 100% viscose derived from bamboo. A first coating may be formed on the fabric by contacting the fabric with an aqueous solution of hypohalide salt such as sodium hypochlorite and optionally an acrylic material. A second coating may be formed on the first coating by contacting the first coating with an aqueous solution of polyethylene glycol epoxide, melamine and optionally polyurethane. The hypohalide salt is stable for at least about three months.

EXPERIMENTAL SECTION

Iodometric Titration Test

The durability of sodium hypochlorite in this new delivery system has been determined by iodimetric titration. In this test, 0.05 g of the new delivery system is dispersed in 40 mL absolute ethanol containing 1.0 wt % acetic acid. One gram of potassium iodide is added, and the mixture is stirred for 1 h at room temperature under $N_2$ atmosphere. The released iodine is titrated with 0.01 mol/L sodium thiosulfate aqueous solution. The same procedure is applied to the same amount of the pure cotton/polyester blend fabric to serve as controls. Percentage chlorine content (indicating sodium hypochlorite content) was calculated according to the following equation:

$$Cl\ \% = \frac{35.5}{2} \times \frac{(V_{Cl} - V_0) \times 10^{-3} \times 0.01}{W_{Cl}},$$

where $V_{Cl}$ and $V_0$ are the volumes (mL) of sodium thiosulfate solutions consumed in the titration of the sample and the control, respectively, and $W_{Cl}$ was the weight (grams) of the sample. Each test is repeated three times, and the average is recorded Example One A piece (50 cm×30 cm) of cotton/polyester blend fabrics (60/40) was dipped into 100 ml aqueous solution containing 2 g of polyethylene glycol epoxide and 0.5 g of melamine for 1 min. The fabric was padded to get 100% of pick up, and was then dried at 120° C. to constant weight. After cooling the fabric to room temperature, 5 ml of a water-based acrylic coating/adhesive solution containing of 2% sodium hypochlorite was sprayed onto the fabric, and then the fabric was air dried over night.

Immediately after treatment, the fabric was found to contain about 2000 parts per million (ppm) of sodium hypochlorite using the iodometric test described above. After three months of exposure to atmosphere at room temperature, the fabric still contained more than about 1800 ppm of sodium hypochlorite, indicating that over about 90 percent of the original sodium hypochlorite remained. The fabric can thus be used for storage and delivery of sodium hypochlorite.

As a comparison example, a piece (50 cm×30 cm) of cotton/polyester blend fabrics (60/40) was directly sprayed with 5 ml of 2% sodium hypochlorite without an initial step of contacting the fabric with an aqueous solution including polyethylene glycol epoxide and melamine. The fabric was air dried over night and then stored in open air at room temperature. Within three days, over 95 percent of the original sodium hypochlorite that was sprayed on the fabric was already lost.

These results suggest that the resin approach is very effective in prolonging the life time of sodium hypochlorite and a wide range of potential applications for storage and delivery of sodium hypochlorite and other inorganic hypochlorite salts and/or hypobromide salts.

Example Two

In another example, a piece (50 cm×30 cm) of bamboo fabric (a knit fabric made of 100% vicose obtained from organic bamboo) was dipped into 100 ml aqueous solution containing 10% of a water-based acrylic coating/adhesive solution with of 2% sodium hypochlorite, and was padded to 100% wet pick up. Five ml of an aqueous solution containing 2% of a water-based polyurethane and 1% of the epoxide/melamine resin was sprayed onto the fabric. The fabric was dried at 40° C. under vacuum to a constant weight. The iodimetric titration test showed that the after this treatment, the fabric contained about 580 ppm of sodium hypochlorite. After two months exposure to atmosphere at room temperature, more than about 540 ppm of sodium hypochlorite remained. This means that over about 90 percent of the originally retained sodium hypochlorite remained. The fabric can thus be used for storage and delivery of sodium hypochlorite.

As a comparison, the same fabric was directly dipped into 2% sodium hypochlorite without applying an aqueous solution including polyurethane, polyethylene glycol epoxide and melamine. The fabric was padded and air dried. After three days in open air at room temperature, greater than 95 percent of the sodium hypochlorite was lost.

Example Three

Ten grams of poly(4-ethylstyrene-co-divinylbenzene) porous beads with a 300-1200 μm particle size and a 100 Å of mean pore size were added into 500 mL sodium hypochloride aqueous solution containing 10% of sodium hypochlorite. One gram of polyethylene glycol (MW: 5000) was added into the mixture, and the mixture was stirred at room temperature for 24 hr to absorb sodium hypochlorite into the pores of the porous beads. The beads were collected by filtration, dried in a vacuum desiccator under dark over night. These beads are defined as sodium hypochlorite-containing beads.

In one example, 1 gram of the above mentioned sodium hypochlorite-containing beads was added into 200 ml of 15 wt % ethylene vinyl acetate (EVA) copolymer solution in dichloromethane. The mixture was stirred for 30 min, and then 10 ml of the mixture were poured into a glass petri dish (10 cm of diameter). After evaporating the solvent in a fume hood, the EVA film containing the beads can be used for storage and delivery of sodium hypochlorite. The iodimetric titration test showed that after treatment, the fabric was found to contain about 2000 parts per million (ppm) of sodium hypochlorite using the iodometric test described above. After three months of exposure to atmosphere at room temperature, over 90 percent (more than 1800 ppm) of the original sodium hypochlorite remained. The fabric can thus be used for storage and delivery of sodium hypochlorite.

In another example, 1 gram of the above mentioned sodium hypochlorite-containing beads was added into 200 ml of a commercial acrylic back coating solution in water. The mixture was stirred for 30 min, and then 10 ml of the mixture were poured onto and then brushed evenly on the back of a piece of acrylic carpet. After drying at room temperature overnight, the carpet can be used for storage and delivery of sodium hypochlorite. The iodimetric titration test showed that after this treatment, the carpet backing contained about 800 ppm of sodium hypochlorite. After three months of exposure to atmosphere at room temperature, over 90 percent (more than about 720 ppm) of the originally retained sodium hypochlorite remained.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A method of delivering storage stable hypohalide salts, the method comprising steps of:
    contacting a material with a first aqueous solution of polyethylene glycol epoxide and melamine, wherein the first aqueous solution consists of 0.1 to 30 grams of polyethylene glycol epoxide and 0.01 to 10 grams melamine per each 100 milliliters of solution;
    drying the first aqueous solution on the material to constant weight to form a first coating consisting of polyethylene glycol and melamine;
    contacting the material with a second aqueous solution including a hypohalide salt; and
    drying the second aqueous solution on the material to form a second coating on the first coating, the second coating comprising the hypohalide salt;
    wherein the material is a fabric.

2. The method of claim 1, wherein the resulting material retains, after about 3 months of atmospheric contact, at least 90 percent of the hypohalide salt originally retained by the material.

3. The method of claim 1, wherein the fabric comprises cellulosic material that includes free hydroxyl, amino, amide, or carboxylate functional groups.

4. The method of claim 1, wherein contacting the material with the first aqueous solution comprises dipping the material into the first aqueous solution or spraying the material with the first aqueous solution.

5. The method of claim 1, wherein the hypohalide salts in the second aqueous solution comprise at least one of hypochlorite salts and hypobromide salts.

6. The method of claim 1, wherein contacting the material with the second aqueous solution comprises dipping the material into the second aqueous solution or spraying the material with the second aqueous solution.

7. An antimicrobial material comprising:
    a fabric,
    a first coating consisting of polyethylene glycol epoxide and melamine; and
    a second coating comprising a hypohalide formed on the first coating.

8. The antimicrobial material of claim 7, wherein the first coating is derived from a first aqueous solution dried on said fabric to constant weight, wherein said first aqueous solution consisting of about 0.1 to about 30 grams of polyethylene glycol epoxide per about 100 milliliter of solution and about 0.01 to 10 grams melamine per about 100 milliliter of solution, the second coating is formed by contacting the first coating with an aqueous solution of hypohalide salts.

9. The antimicrobial material of claim 7, wherein the fabric comprises cellulosic material that includes free hydroxyl, amino, amide, or carboxylate functional groups.

10. The antimicrobial material of claim 7, wherein the hypohalide salts are selected from sodium hypochlorite, calcium hypochlorite, sodium hypobromide, calcium hypobromide, and combinations thereof.

11. The antimicrobial material of claim 7, wherein the first coating consists of about 13.3 grams polyethylene glycol epoxide and about 3.3 grams melamine of per square meter of fabric.

12. The antimicrobial material of claim 8, wherein the first aqueous solution consists of about 2 grams of polyethylene glycol epoxide and about 0.5 grams melamine per about 100 milliliter of solution.

13. The antimicrobial material of claim 7, wherein the fabric contains about 2000 parts per million (ppm) of sodium hypochlorite.

\* \* \* \* \*